United States Patent [19]
Lee et al.

[11] Patent Number: 6,090,413
[45] Date of Patent: Jul. 18, 2000

[54] PROCESS OF PROLONGING ORGAN ALLOGRAFT SURVIVAL

[76] Inventors: Timothy D. Lee, 6895 Churchill Drive, Halifax, Nova Scotia, Canada, B3L 1E8; Vivian G. McAlister, 6161 Oakland Road, Halifax, Nova Scotia, Canada, B3H 1P3

[21] Appl. No.: 08/913,622

[22] PCT Filed: Mar. 23, 1995

[86] PCT No.: PCT/IB96/00400

§ 371 Date: Oct. 29, 1997

§ 102(e) Date: Oct. 29, 1997

[87] PCT Pub. No.: WO96/29082

PCT Pub. Date: Sep. 26, 1996

[51] Int. Cl.$^7$ ............................................ A61K 35/56
[52] U.S. Cl. .............................................. 424/520; 424/572
[58] Field of Search ............................ 424/520, 572; 800/2, DIG. 5

[56] References Cited

FOREIGN PATENT DOCUMENTS

| 045 237 | 2/1982 | European Pat. Off. . |
|---|---|---|
| WO 93 17698 | 9/1993 | WIPO . |
| WO 95 24425 | 9/1995 | WIPO . |

OTHER PUBLICATIONS

N.E. Street et al., Faseb Journal for Experimental Biology, "Functional Diversity of T Lymphocytes Due to Secretion of Different Cytokine Patterns", vol. 5, No. 2, pp. 174, Feb. 1991.
A. Sher et al., Journal of Immunology, "Production of Il–10 by CD4+ Lymphocytes correlates with Down–Regulation of Th1 Cytokine Synthesis in Helminth Infection", vol. 147, No. 8, pp. 2713–2716, Oct. 15, 1991.
Bradley et al., Mayo Clin Proc 53:332–335, 1978.
Krenger et al., Transplantation, 58(11):1251–1257, Dec. 15, 1994.
Barriga, Immunology, 34:167–173, 1978.
Caulada–Benedetti et al., Journal of Immunology, 146(5):1655–1660, Mar. 1, 1991.
Kupiec–Weglinski et al., Journal of Immunology, 151(9):5053–5061, Nov. 1, 1993.
Grzych et al., Journal of Immunology, 146(4):1322–1327, 1991.
Else et al., Parasite Immunology 15(10): 595–600 (1993).
Jenkins et al., Transactions of the Royal Society of Tropical Medicine and Hygeine 88(3): 269–273 (1994).
Mazumder et al., Indian Journal of Gastroenterology 11(3): 117–120 (1992).
Hogaboam et al., Journal of Lipid Mediators 4(2): 211–224 (1991).
Lee et al., Immunology 47: 227–232 (1982).
Ishikawa et al., Parasite Immunology 16: 181–186 (1994).
Mayberry et al., Journal of Parasitology 79(6): 962–963 (1993).
Allen et al., International Archives of Allergy and Immunology 109(1): 3–10 (1996).
Else et al., Immunology 72: 508–513 (1991).
Fahey, Basic Concepts of Organ Procurement, Perfusion and Preservation for Transplantation, Academic Press, New York, 1992.
The Merck Manual of Diagnosis and Therapy, Merck & Co., Rahway, NJ, 1992.
Allen et al., Parasite Immunology 20: 241–247 (1998).

*Primary Examiner*—Jean C. Witz
*Attorney, Agent, or Firm*—Bereskin & Parr

[57] ABSTRACT

The present invention provides a process of prolonging organ allograft survival in an organism comprising down-regulating Th1 activity in the organism. The down-regulation of Th1 activity is accomplished either by infecting the organism with an effective Th2 up-regulating amount of a nematode or by administering to the organism an effective Th2 up-regulating amount of a soluble extract of a nematode. Exemplary and preferred nematodes for use in a process of the present invention are of the genus Nipostrongylus, Trichuris, Ascaris or Caenorhabditis. Most preferred is the nematode *Nipostrongylus brasiliensis*. A process of the present invention is particularly useful in prolonging kidney allograft survival.

6 Claims, 1 Drawing Sheet

Total IgG1

6,090,413

PROCESS OF PROLONGING ORGAN ALLOGRAFT SURVIVAL

TECHNICAL FIELD OF THE INVENTION

The field of the present invention is organ allograft survival. More specifically, the field of the present invention is prolongation of organ allograft survival. Organ allograft survival is prolonged by down-regulating Th1 activity in an organism receiving an organ allograft.

BACKGROUND OF THE INVENTION

The development of novel immunosuppressive drugs has caused a dramatic increase in the short term survival of organ transplants in recent years. The use of such drugs, however, is associated with side effects such as opportunistic infections, tumors and ultimately, chronic rejection.

The recent description of two subsets of T helper cells (Th), with different cytokine secretion profiles and activities, may provide a new paradigm for immunoregulation of organ allograft rejection (Mosmann et al., *Immunol. Today*, 8:223, 1987). The two Th cell subsets, designated Th1 and Th2, can be characterized on the basis of their respective cytokine production profiles. Th1 cells produce and secrete interferon-gamma (IFN-γ), lymphotoxin (LT) and interleukin-2 (IL-2). On the other hand, Th2 cells produce and secrete interleukin-4 (IL-4), interleukin-5 (IL-5), interleukin-6 (IL-6) and interleukin-10 (IL-10).

Acute organ allograft rejection may result from responses associated with the pro-inflammatory cytokines IL-2, IFN-γ, and TNF-α, derived from Th1 cells. Down-regulation of Th1 activity, therefore, may be a useful immunomodulatory therapy. It is also well known that infection by certain parasitic organisms can modulate the balance between Th1 and Th2 activity. By way of example, Sher and coworkers have demonstrated that a depression of Th1-type responses can be achieved by helminth infection (Sher et al., *J. Immunol.*, 147:2713, 1991). Helminth infection can also result in up-regulation or stimulation of Th activity. Nematode induced up-regulation can encompass stimulation of IgE (and IgG1 in mice or IgG4 in humans), mast cell hyperplasia and eosinophilia in all species, including humans.

It is well known that the immune modulation associated with helminth infection is unrelated to the worm antigens per se. For example, greater than 80 percent of the IgE generated during *Nipostrongylus brasiliensis* (*N. brasiliensis*) infection was found not to be directed to *N. brasiliensis* (Jarrett et al., *Clin. Exp. Immunol.*, 24:326, 1976).

Such induced up-regulation may be due to the cross-regulatory actions of the Th1/Th2 system. The Th1 and Th2 subsets have been found to be cross-regulatory with respect to differentiation and activity. By way of example, cytokines produced by Th2 cells (e.g., IL-4 and IL-10) inhibit Th1 cell growth and cytokine production and ablate the effects of Th1 cytokines (e.g., IFN-γ) on their targets, while IFN-γ inhibits Th2 function (Powrie et al., *Immunol. Today*, 14:270, 1993).

The concept of resistance or susceptibility being related to Th1/Th2 balance has also been suggested in a variety of other models, including AIDS, and even successful pregnancy. The finding of pro-inflammatory cytokines IL-2, IFN-γ, TNF-α and IL-6 in rejecting kidney allografts lends support to the hypothesis that Th1-type T cells orchestrate the immune response, which culminates in rejection. It likely that a Th1/Th2 balance is established within the graft which changes over time, differs among individuals, and is dependent on the treatment administered but that the cellular mechanisms behind graft rejection, such as infiltration by macrophages and CTL, are consistent with the activities of Th1 cells.

BRIEF SUMMARY OF THE INVENTION

In one aspect, the present invention provides a process of prolonging organ allograft survival in an organism comprising down-regulating Th1 activity in the organism.

In a preferred embodiment, the down-regulation of Th1 activity is accomplished by infecting the organism with an effective Th2 up-regulating amount of a nematode.

In another preferred embodiment, the down-regulation of Th1 activity is accomplished by administering to the organism an effective Th2 up-regulating amount of a soluble extract of a nematode.

Exemplary and preferred nematodes for use in a process of the present invention are of the genus Nippostrongylus, Trichuris, Ascaris or Caenorhabditis. More preferred are *Nippostrongylus brasiliensis*, *Trichuris muris*, *Trichuris suis*, *Ascaris lumbricoides*, *Ascaris suum* or *Caenorhabditis elegans*. Most preferred is *Nippostrongylus brasiliensis* (*N. brasiliensis*). A process of the present invention is particularly useful in prolonging kidney allograft survival.

BRIEF DESCRIPTION OF THE DRAWINGS

In the drawing, which forms a portion of the specification.

DETAILED DESCRIPTION OF THE INVENTION

I. The Invention

Figure 1:
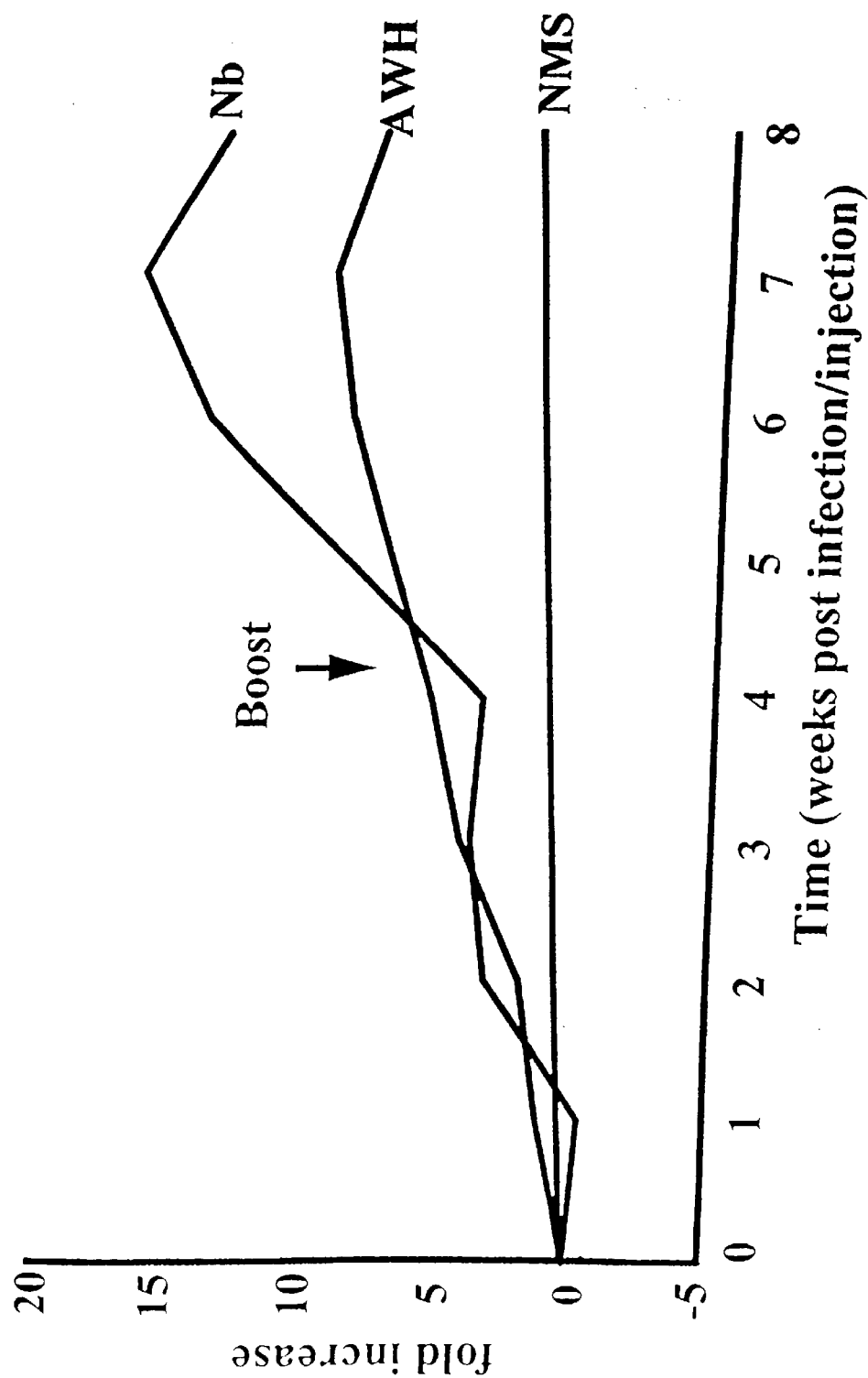
FIG. 1 shows IgG1 levels following *N. brasiliensis* infection or treatment with *N. brasiliensis* extract.

Infection with parasites such as nematodes induces strong IgE responses not restricted to parasite antigens. In addition, certain helminths have profound immunomodulatory effects on infected animals, inducing strong Th2 responses while diminishing Th1 activity. The present invention provides that infection of organisms with nematodes or the administration of soluble nematode extracts to organisms significantly prolonged organ allograft survival in those organisms.

II. Process of Prolonging Allograft Survival

In one aspect, the present invention provides a process of prolonging organ allograft survival in an organism comprising down-regulating Th1 activity in the organism.

As used herein, the phrase "organ allograft" means a body organ graft from a donor organism of the same species but a different genotype than the recipient organism. As used herein, the term "organ" means a vascularized internal organ such as heart, liver and kidney. An exemplary and preferred organ allograft is a kidney allograft. As used herein, an organ does not include skin. Skin differs from vascularized organs contemplated by the present invention because a substantial component of the graft vascular supply is derived from the donor rather than the recipient. Thus, skin allografts are much less susceptible to certain immune-mediated injuries (Bradley et al., *Immunol. Today*, 13:434, 1992).

As used herein, the terms "up-regulation" and "down-regulation" and their grammatical equivalents mean, respectively, stimulation and inhibition. Thus, down-regulation of Th1 activity means a depression or inhibition of the cascade of physiological responses that accompany a T1 cytokine production profile and up-regulation of Th2 activity means a stimulation or enhancement of the cascade of physiological responses that accompany a Th2 cytokine production profile.

In a preferred embodiment, the down-regulation of Th1 activity is accomplished by infecting the organism with an effective Th2 up-regulating amount of a nematode. An effective amount is that amount necessary to bring about the desired effect (e.g., down-regulation of Th1 activity). Means for determining an effective amount are well known in the art. By way of example, an organism is infected with various amounts of a particular nematode and the level of Th1 activity monitored. An effective amount will depend inter alia, as is well known in the art, on the nature of the organism being injected and the nature of the particular nematode used. Exemplary effective amounts using rodents and the nematode N. brasiliensis are set forth hereinafter in the Examples.

In another preferred embodiment, the down-regulation of Th1 activity is accomplished by administering to the organism an effective Th2 up-regulating amount of a soluble extract of a nematode. As set forth above, means for determining an effective amount of a soluble extract are well known and readily ascertainable by a skilled artisan. Means for making a soluble extract are also well known in the art (See, e.g., Lee et al., *Immunology*, 55:721, 1985). By way of example, nematodes are homogenized in an aqueous medium such as saline (0.9% NaCl). The medium can further comprise buffers such as phosphate. Homogenization can be accomplished by mechanical means or other disruptive means such as sonication. The homogenate is typically cleared of particulate matter using ultracentrifugation. The nematode is then filter sterilized to remove bacteria.

A soluble nematode extract can be administered to the organism by parenteral routes of administration as is well known in the art. The extract can be dispersed or suspended in a physiologically acceptable diluent prior to administration. A preferred route of administration is subcutaneous. An extract can be administered prior to, simultaneously with or after organ transplantation. In a preferred embodiment, an extract is administered prior to, simultaneously with and after transplantation. One of ordinary skill in the art can readily determine the optimum administration schedule for a given transplant and treatment regimen.

Any nematode that down-regulates Th1 activity can be used in a process of the present invention. Exemplary and preferred nematodes for use in a process of the present invention are of the genus Nippostrongylus, Trichuris, Ascaris or Caenorhabditis. More preferred are *Nippostrongylus brasiliensis, Trichuris muris, Trichuris suis, Ascaris lumbricoides, Ascaris suum* or *Caenorhabditis elegans*. Most preferred is *Nippostrongylus brasiliensis* (*N. brasiliensis*).

A process of the present invention prolongs allograft survival when compared to allograft survival performed in the absence of nematode treatment. In other words, a process of the present invention improves or increases survival time of the allograft.

A detailed description of the use of a process of the present invention to prolong kidney allograft survival is set forth hereinafter in the Examples. Briefly, rats were infected with *N. brasiliensis* (Nb) or treated with a soluble extract of *N. brasiliensis* (Nb extract) and received a kidney allograft. The survival time of the kidney allograft was increased from 9.7±1.2 days (no treatment) to 32.0±10.0 days (Nb infection) and 21.5±4.6 days (Nb extract treatment). By day 5 post transplant, untreated allografts contained a substantial mononuclear cell infiltrate and kidney destruction was advanced. In contrast, kidneys transplanted into Nb treated animals had only a mild cellular infiltrate and retained normal architecture. FACS analysis revealed a significant decrease in the number of CD8+ cells infiltrating Nb treated grafts. Preliminary RT-PCR analysis of mRNA expression by graft-infiltrating cells indicated that the production of IL-4 was up-regulated in Nb-treated kidneys as opposed to untreated allografts.

In additional studies, Nb treatment was associated with substantial and significant increases in IgG1 levels (See Example 2).

The following Examples illustrate preferred embodiments of the present invention and are not limiting of the claims or specification in any way.

EXAMPLE 1

Kidney Allograft Survival

Lewis (LEW,RT1[1]) and Brown Norway (BN, RT1") rats were chosen as recipients and donors, respectively. Male rats were purchased from Harlan Sprague Dawley (Indianapolis, IN) and provided with water and rat chow ad libitum. Animals receiving a *N. brasiliensis* infection were injected with 3500 third stage infective larvae subcutaneously four days prior to transplantation. Animals receiving the nematode products were injected subcutaneously, at day −4, 0 and +4 (with day 0 being the day of transplant) with 200 worm equivalents of adult worm homogenate. All procedures were performed under sodium pentobarbital anaesthesia (65 mg/kg).

The left kidney of the donor (BN) rat was perfused in situ with cold (4° C.) saline, mobilized, and removed. It remained in cold saline during the preparation of the recipient. Following left nephrectomy of the Lewis recipient, the BN kidney was transplanted in a heterotopic position. Ureteric reconstruction in these experiments was achieved by end-to-end anastomosis. Four days after the transplants, the recipients were re-anaesthetized and a right native nephrectomy was performed. Animals were sacrificed when they showed signs of morbidity due to failure of the transplanted kidney.

Graft survival data are shown below in Table 1.

TABLE 1

| Kidney Allograft Survival Following Nematode Infection | | |
| --- | --- | --- |
| Treatment | Survival (days) | Mean ± SD |
| No treatment | 10, 8, 11, 11 9, 8, 11, 9, 10 | 9.7 ± 1.2 |
| No infection | 34, 27, 34, 23 25, 34, 25, 54 | 32.0 ± 10.0 |
| No extract | 30, 21, 22, 20 16, 20 | 21.5 ± 4.6 |

These results clearly show a significant prolongation of kidney allograft survival in animals given either a *N. brasiliensis* infection or soluble worm extract. In untreated animals kidneys survived a mean of only 9.7±1.2 (mean±SD, n=9) days, whereas kidneys in nematode infected rats retained functional capacity much longer, resulting in a mean survival time of 32.0±10.0 (mean+DS, n-8) days, with one animal retaining grafted kidney function up to 54 days post transplant. In animals treated with the worm extract the survival was also significantly longer (mean 21.5±4.6).

In addition to graft survival the histological appearance of the transplanted kidneys was assessed in the control versus *N. brasiliensis* treated recipients 5 days after transplant. Transplanted kidneys were flushed with cold saline and cut into 2–3 mm thick slices before fixation in formalin. Sections were taken and stained with hematoxylin and eosin using standard protocols.

The results demonstrate clear differences between the kidneys taken from the *N. brasiliensis* infected and the control groups. The intensity of the infiltration was, in a blinded evaluation, found to be much more extensive in the control group when compared to the *N. brasiliensis* infected group. In the control group, there was extensive infiltration of the interstitia by mononuclear cells and evidence of damage to the tubular endothelium in some tubules. In the kidneys isolated from *N. brasiliensis* infected recipients, in contrast, there was only a small amount of mononuclear infiltrate around major vessels and almost no interstitial infiltrate. Kidney architecture in the *N. brasiliensis* infected recipients was virtually normal.

These data show that infection of rats by the nematode *N. brasiliensis* or treatment with *N. brasiliensis* extracts significantly prolonged kidney allograft survival across a known strong histocompatibility barrier.

This prolongation likely results from the ability of *N. brasiliensis* to strongly activate Th2 responses with a resultant inhibition of Th1 activity.

EXAMPLE 2
Regulation Of IgG1 Response By Nematodes

Increases in the serum levels of total (non-specific) IgE and IgG1 or IgG4 are associated with nematode infections in mice and humans respectively. There are several points where this response can be regulated. One of such, is during the process of Immunoglobulin class switch.

A group of five BALB/c mice was infected with 500 infective larvae of the nematode *Nippostrongylus brasiliensis* and a second group of five BALB/c mice (age matched) was injected subcutaneously with an extract from *N. brasiliensis* (Adult Worm Homogenate, AWH) at a concentration of 200 worm equivalent emulsified in Freund's Incomplete Adjuvant. The levels of total IgG1 in the serum obtained from the blood taken from these mice, were measured weekly for ten weeks, by IgG1 capture ELISA.

The data showed clearly that, the nematode extract AWH induces significant increases in the production of total serum IgG1. The result agrees with the massive increase in total IgE and IgG1 levels associated with infection with the larvae. As shown in FIG. 1, a ten fold increase in the IgG1 levels was observed. Prior to the injection of AWH, the total serum IgG1 level in the mice was 0.25 mg/ml. This level increased continuously from week 1 (0.30 mg/ml) through week 4 (1.15 mg/ml). Further increases in the serum IgG1 level upon re-injection with the nematode extract at week 4, were also observed. It reached its maximum (2.15 mg/ml) at week 7, before it started to decline. *N. brasiliensis* extract AWH, also induced significant increase in total IgG1 levels in vivo.

What is claimed is:

1. A process of prolonging organ allograft survival in an organism comprising down-regulating Th1 activity in the organism by administering to the organism an effective Th2 up-regulating amount of a soluble extract from a nematode from the genus Nipposirongylus.

2. The process according to claim 1 wherein the nematode is *Nippostrongylus brasiliensis*.

3. The process according to claim 1 wherein the organ is kidney.

4. A process of prolonging organ allograft survival in an organism comprising administering to the organism an effective amount of a soluble extract from a nematode from the genus Nippostrongylus .

5. The process according to claim 4 wherein the nematode is *Nippostrongylus brasiliensis*.

6. The process according to claim 4 wherein the organ is kidney.

* * * * *